(12) United States Patent
Jackson

(10) Patent No.: US 7,121,496 B2
(45) Date of Patent: Oct. 17, 2006

(54) METHOD AND SYSTEM FOR CORRECTING WEB DEFORMATION DURING A ROLL-TO-ROLL PROCESS

(75) Inventor: Warren Jackson, San Francisco, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 304 days.

(21) Appl. No.: 10/692,973

(22) Filed: Oct. 23, 2003

(65) Prior Publication Data

US 2005/0087578 A1    Apr. 28, 2005

(51) Int. Cl.
*B65H 43/00* (2006.01)
(52) U.S. Cl. .................................. 242/563.1
(58) Field of Classification Search ............ 242/563.1; 226/31
See application file for complete search history.

(56) References Cited

U.S. PATENT DOCUMENTS

| | | | | |
|---|---|---|---|---|
| 4,021,031 A | * | 5/1977 | Meihofer et al. | 242/563.1 |
| 4,054,251 A | * | 10/1977 | Henderson et al. | 242/563.1 |
| 4,485,982 A | * | 12/1984 | St. John et al. | 242/563.1 |
| 4,610,739 A | | 9/1986 | Jensen | |
| 5,954,292 A | * | 9/1999 | Nawano et al. | 242/563.1 |
| 6,450,383 B1 | * | 9/2002 | Crowley et al. | 226/31 |
| 6,519,866 B1 | | 2/2003 | Gerdes | |

* cited by examiner

*Primary Examiner*—William A. Rivera

(57) ABSTRACT

The present invention includes a method and system for correcting web deformation during a roll-to-roll process. The present invention includes controllable mechanical components that are capable of dynamically adjusting the planarity of the web during the roll-to-roll process. By adjusting the web during the roll-to-roll process, the accuracy of the layer-to layer alignment of successive patterning steps is greatly increased thereby enabling the production of electronic structures with lower overlap capacitance and higher resolution. A first aspect of the present invention is a method for correcting web deformation during a roll-to-roll process. The method includes initiating a roll-to-roll process involving a flexible web substrate, detecting deformation in the flexible web substrate during the roll-to-roll process and dynamically aligning the flexible web substrate based on the detected deformation.

22 Claims, 8 Drawing Sheets

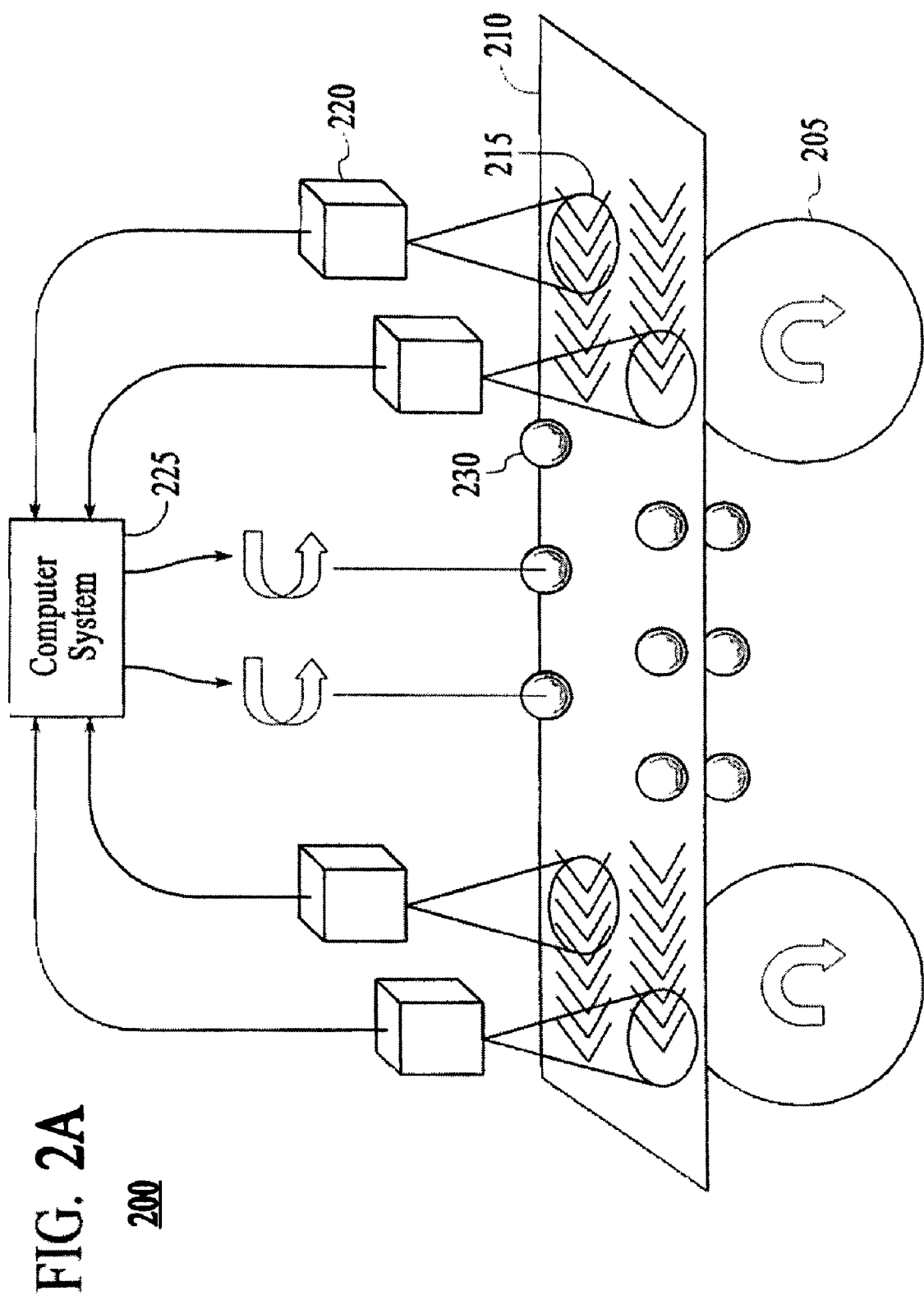

METHOD AND SYSTEM FOR CORRECTING WEB DEFORMATION DURING A ROLL-TO-ROLL PROCESS

FIELD OF THE INVENTION

The present invention relates generally to semiconductor processing and more particularly to a method and system for correcting web deformation during a roll-to roll process.

BACKGROUND OF THE INVENTION

In the semiconductor processing industry, there is currently a strong trend toward downsizing existing structures and fabricating smaller structures. This process is commonly referred to as microfabrication. One area in which microfabrication has had a sizeable impact is in the microelectronic area. In particular, the downsizing of microelectronic structures has generally allowed the structures to be less expensive, have higher performance, exhibit reduced power consumption, and contain more components for a given dimension. Although microfabrication has been widely active in the electronics industry, it has also been applied to other applications such as biotechnology, optics, mechanical systems, sensing devices and reactors.

Typically the fabrication of an electronic device will require several patterning steps that often must be aligned with each other with a degree of accuracy approaching or even exceeding the minimum feature size. Currently, electronic devices are fabricated on flat, inflexible, nondeformable substrates such as crystalline Si or glass using photolithography. However, a much more inexpensive means for producing such devices is based on imprint lithography.

Imprint lithography is typically utilized to pattern thin films on a substrate material with high resolution using contact between a master with the features of the structure to be fabricated and the substrate material to be patterned. The thin films patterned can be dielectrics, semiconductors, metals or organic and can be patterned as thin films or individual layers. Imprint lithography is particularly useful in roll-to-roll processing since it has a higher throughput and can handle wider substrates. This roll-to-roll substrate will be referred to as a web in the subsequent discussion.

In conventional photolithography, optical alignment marks are used to guarantee alignment between successive patterning steps. Although, it is possible to use optical alignment marks in a roll-to-roll process it is not practical for several reasons. First, it adds additional complexity since the fundamental imprint lithography process is not optical. Next, the lack of planarity of the substrate in a roll-to-roll environment causes difficulties in the accuracy with which optical alignments can be made due to depth of field restrictions and other optical aberrations. Finally, the flexible substrates used in roll-to-roll processing may experience dimensional changes due to variations in temperature, humidity, or mechanical stress. These deformations and/or dilations of one patterned layer with respect to the next may make accurate alignments over a large area impossible.

Accordingly, what is needed is a method and system for correcting web deformation during a roll-to-roll process. The method and system should be simple, inexpensive and capable of being easily adapted to existing technology. The present invention addresses these needs.

SUMMARY OF THE INVENTION

The present invention includes a method and system for correcting web deformation during a roll-to-roll process. The present invention includes controllable mechanical components that are capable of dynamically adjusting the planarity and dimensions of the web during the roll-to-roll process. By adjusting the web dimensions during the roll-to-roll process, the accuracy of the layer-to-layer alignment of successive patterning steps is greatly increased thereby enabling the production of complex electronic structures with lower overlap capacitance and higher resolution.

A first aspect of the present invention is a method for correcting web deformation during a roll-to-roll process. The method includes initiating a roll-to-roll process involving a flexible web substrate, detecting deformation in the flexible web substrate during the roll-to-roll process and dynamically aligning the flexible web substrate based on the detected deformation.

A second aspect of the present invention is a roll-to-roll processing system. The processing system includes a web rolling mechanism, a flexible web substrate coupled to the web rolling mechanism, a plurality of sensors configured to dynamically detect deformation in the flexible web substrate, at least one controllable mechanical component coupled to the flexible web substrate and a computer system coupled to the plurality of sensors and the at least one controllable mechanical component wherein the computer system includes logic for detecting deformation in the flexible web substrate and dynamically aligning the flexible web substrate based on the detected deformation.

Other aspects and advantages of the present invention will become apparent from the following detailed description, taken in conjunction with the accompanying drawings, illustrating by way of example the principles of the invention.

BRIEF DESCRIPTION OF THE DRAWINGS

The drawings referenced herein form a part of the specification. Features shown in the drawing are meant as illustrative of only some embodiments of the invention, and not of all embodiments of the invention, unless otherwise explicitly indicated, and implications to the contrary are otherwise not to be made.

FIG. 2A is an illustration of a system in accordance with an embodiment of the present invention.

DETAILED DESCRIPTION

Figure 1A:
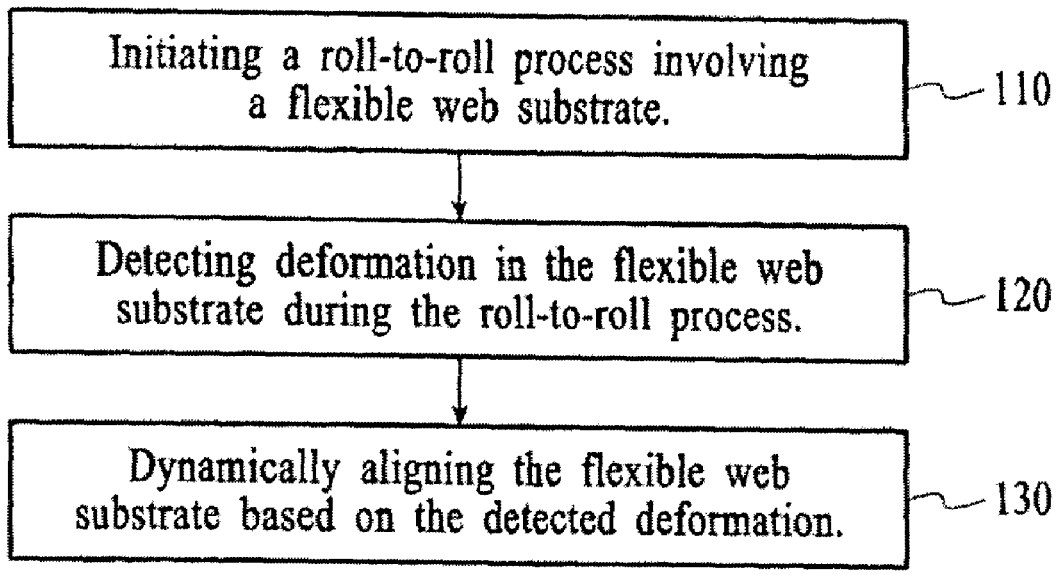
FIG. 1A is a high-level flow chart of a method in accordance with an embodiment of the present invention.

The present invention relates to a method and system for correcting web deformation during a roll-to-roll process. The following description is presented to enable one of ordinary skill in the art to make and use the invention and is provided in the context of a patent application and its requirements. Various modifications to the embodiments and the generic principles and features described herein will be readily apparent to those skilled in the art. Thus, the present invention is not intended to be limited to the embodiment shown but is to be accorded the widest scope consistent with the principles and features described herein.

As shown in the drawings for purposes of illustration, the present invention is a method and system for correcting web deformation during a roll-to-roll process. The present invention includes controllable mechanical components that are capable of dynamically adjusting the planarity of the web during the roll-to-roll process. By adjusting the web during the roll-to-roll process, the accuracy of the layer-to layer alignment of successive patterning steps is greatly increased thereby enabling the production of electronic structures with lower overlap capacitance and higher resolution.

FIG. 1A is a high level flow chart of an exemplary method for correcting web deformation. A first step 110 includes initiating a roll-to-roll process involving a flexible web substrate. A second step 120 includes detecting deformation in the flexible web substrate during the roll-to-roll process. A final step 130 includes dynamically aligning the flexible web substrate based on the detected deformation. Because the alignment process affects the web deformation state, the effects of the alignment process affect the web deformation detected by step 120. Thus, the web deformation state is corrected by a closed feedback system.

In an embodiment, step 120 involves the implementation of optical marks on the flexible web substrate to detect the deformation. The detected deformation state of the web can then be compared to a desired deformation state. Based on this comparison an error signal is generated. From this error signal and knowledge about the effects of the actuators on the deformation state of the web, a deformation state correction signal can be generated and utilized to dynamically align the flexible web substrate.

Figure 1B:
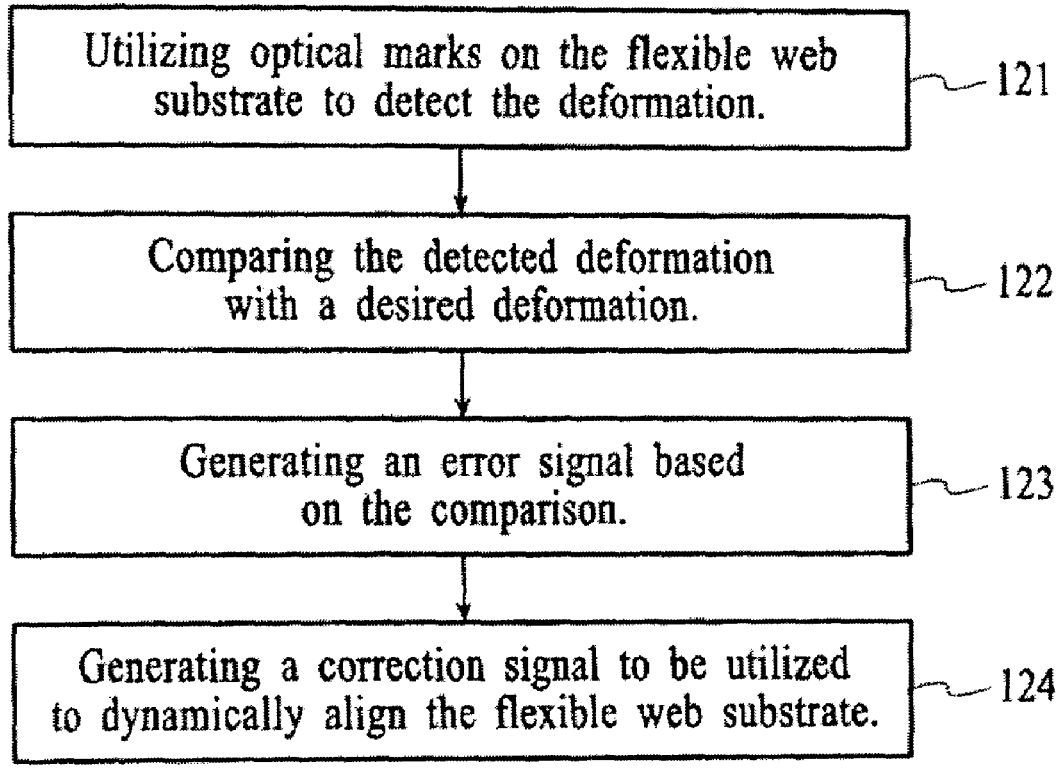
FIG. 1B is a more detailed flowchart of steps that could be utilized to detect deformation on a flexible web substrate in accordance with an embodiment of the present invention.

FIG. 1B is a more detailed flowchart of steps that could be utilized to detect deformation on a flexible web substrate in accordance with an embodiment of the present invention. A first step 121 includes utilizing optical marks on the flexible web substrate to detect the deformation. A second step 122 includes comparing the detected deformation with a desired deformation. A next step 123 involves generating an error signal based on the comparison. A final step 124 includes generating a correction signal to be utilized to dynamically align the flexible web substrate.

The above-described embodiment of the invention may be implemented, for example, by operating a computer system to execute a sequence of machine-readable instructions. In particular, conversion of the deformation measurements provided by the deformation detection, comparing the deformation to the desired state, generating an appropriate error signal to correct the error, and conversion of the deformation correction signal to appropriate signals to the deformation adjustment are beneficially implemented within said computer system. The instructions may reside in various types of computer readable media. In this respect, another aspect of the present invention concerns a programmed product, comprising computer readable media tangibly embodying a program of machine-readable instructions executable by a digital data processor to perform the method in accordance with an embodiment of the present invention.

This computer readable media may comprise, for example, RAM contained within the system. Alternatively, the instructions may be contained in another computer readable media and directly or indirectly accessed by the computer system. Whether contained in the computer system or elsewhere, the instructions may be stored on a variety of machine readable storage media, such as a Direct Access Storage Device (DASD) (e.g., a conventional "hard drive" or a RAID array), magnetic data storage diskette, magnetic tape, electronic non-volatile memory, an optical storage device (for example, CD ROM, WORM, DVD,), or other suitable computer readable media including transmission media such as digital, analog, and wireless communication links. In an illustrative embodiment of the invention, the machine-readable instructions may comprise lines of compiled C, C++, or similar language code commonly used by those skilled in the programming for this type of application arts.

FIG. 2A is a high-level illustration of a system 200 for correcting web deformation. The system 200 includes web rollers 205, a flexible substrate or web 210, web position sensors 220 and controllable mechanical components 230. The flexible web substrate is a polymeric material such as polyamide, polyethylene terephthalate, polyether sulfone, polycarbonate, polyarylate, and polyethylene naphthalate or an inorganic material such as very thin glasses or laminates of two or more such materials. Although these materials are disclosed, one of ordinary skill in the art will readily recognize that a variety of different materials are capable of being implemented.

Figure 2B:
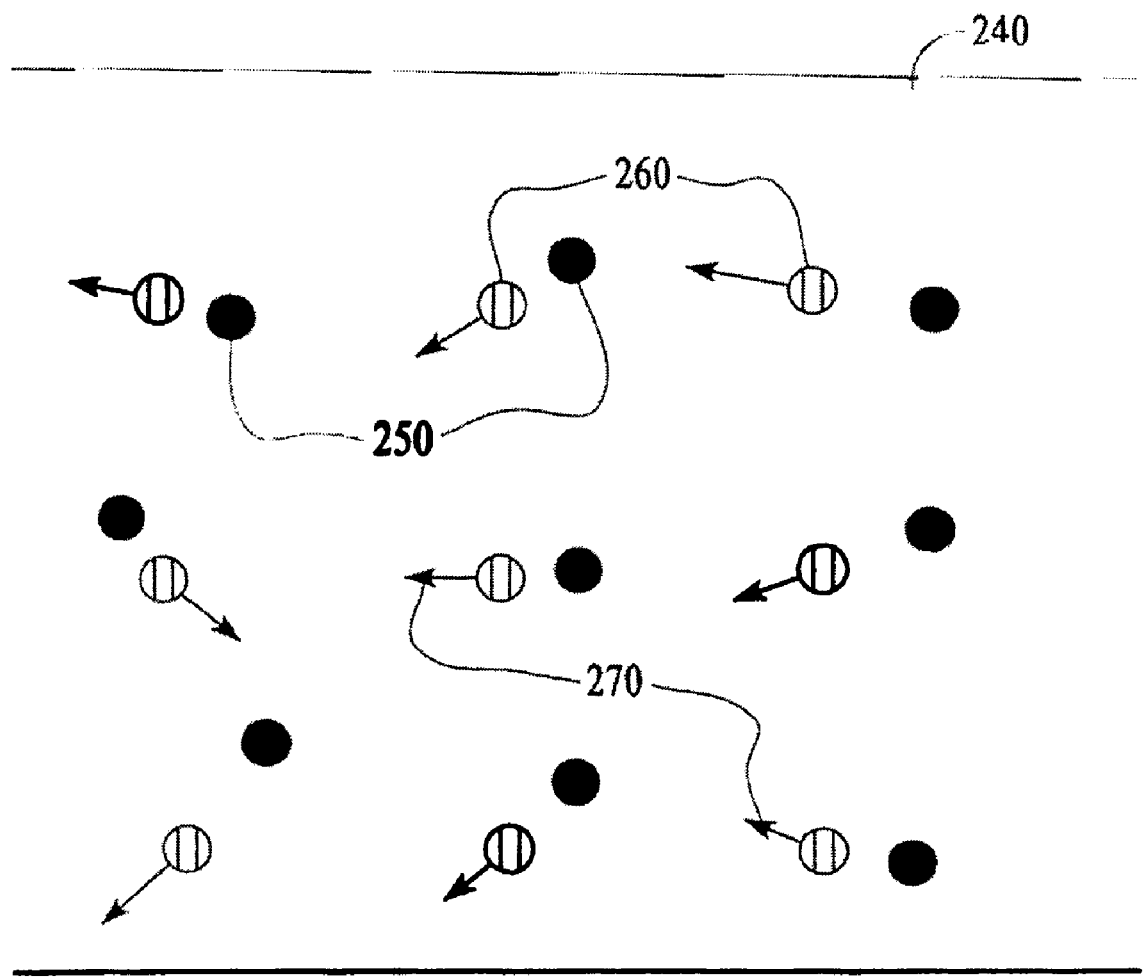
FIG. 2B shows a possible embodiment for determining the needed deformation corrections in accordance with an embodiment of the present invention.

FIG. 2B shows an embodiment for determining deformation corrections. FIG. 2B shows a web 240. Items 250 represent the actual position of optical points on the web 240 and items 260 represent the desired positions of the optical points. Accordingly, items 270 represent the displacement that is needed to bring the actual positions 250 of the optical markings to the desired positions 260. Accordingly, if such displacements are imposed on the web 240, then the rest of the features of the web 240 should be in near alignment as well.

Figure 3:
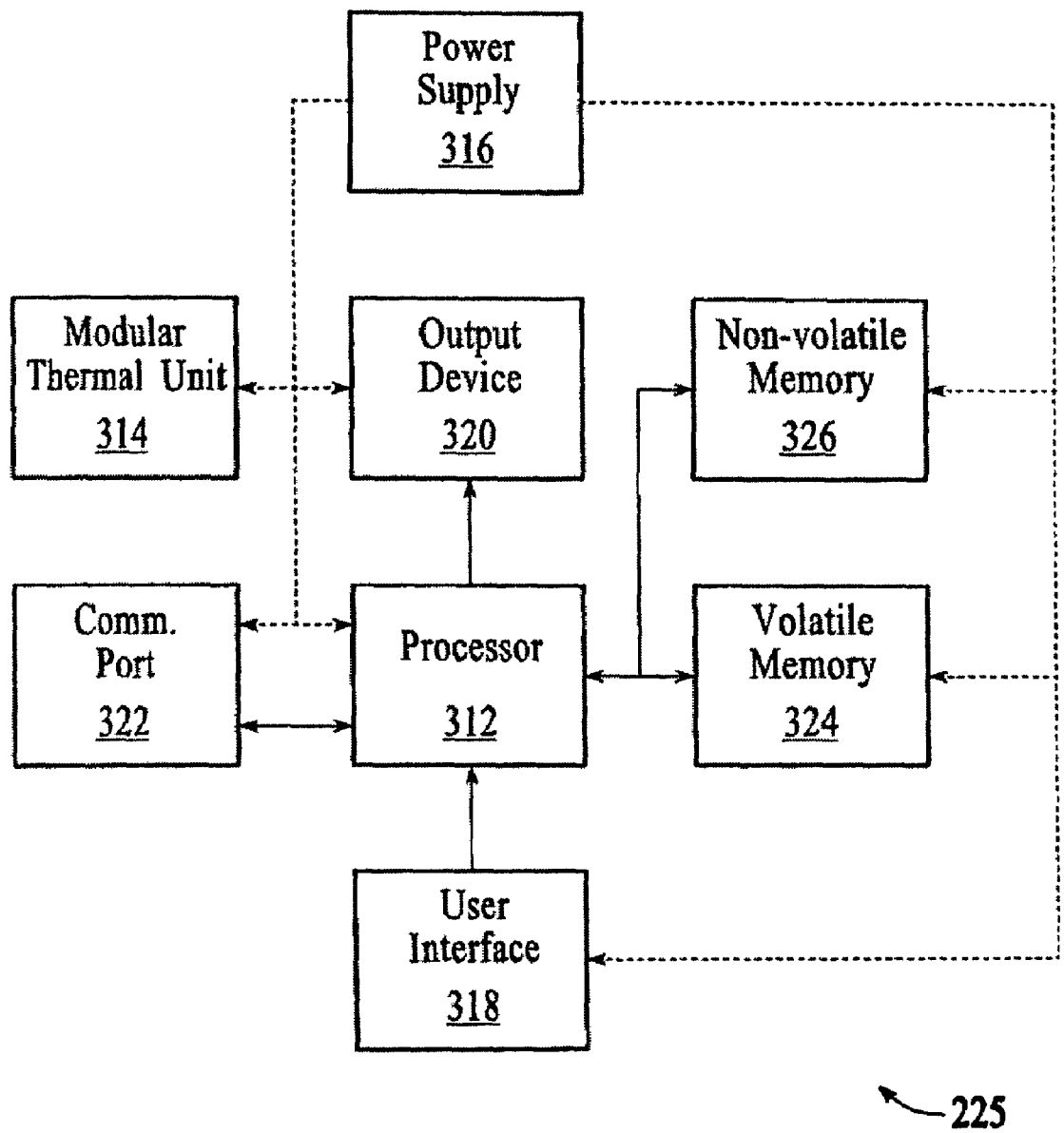
FIG. 3 is a block diagram of a computer system that could be utilized in conjunction with an embodiment of the present invention.

Referring back to FIG. 2A, the web position sensors 220 and the controllable mechanical components 230 are electronically coupled to a computer system 225. For an example of such a computer system, please refer to FIG. 3. In FIG. 3, a block diagram of a computer system, generally designated by the reference numeral 225, is featured. Computer 225 may be any of a variety of different types, such as a notebook computer, a desktop computer, an industrial personal computer, an embedded computer, etc. In the illustrated embodiment, a processor 312 controls the functions of computer system 225. In this embodiment, data, as illustrated by the solid line, is transferred between the processor 312 and the components of system 225. Additionally, a modular thermal unit 314 is used to remove heat from the processor 312. Computer 225 also includes a power supply 316 to supply electrical power, as illustrated by the dashed line, to the components of computer system 225. Additionally, power supply 316 may include a battery.

Computer system 225 may incorporate various other components depending upon the desired functions of computer 225. In the illustrated embodiment, a user interface 318 is coupled to processor 312. Examples of a user interface 318 include a keyboard, a mouse, and/or a voice recognition system. Additionally, an output device 320 is coupled to processor 312 to provide a user with visual information. Examples of an output device 320 include a computer monitor, a television screen, a printer or the like. In this embodiment a communications port 322 is coupled to processor 312 to enable the computer system 225 to communicate with an external device or system, such as a printer, another computer, or a network.

Processor 312 utilizes software programs to control the operation of computer 225. Electronic memory is coupled to processor 312 to store and facilitate execution of the programs. In the illustrated embodiment, processor 312 is coupled to a volatile memory 324 and non-volatile memory 326. A variety of memory types, such as DRAMs, SDRAMs, SRAMs, etc., may be utilized as volatile memory 324. Non-volatile memory 326 may include a hard drive, an optical storage, or another type of disk or tape drive memory. Non-volatile memory 326 may include a read only memory (ROM), such as an EPROM, to be used in conjunction with volatile memory 324.

The system 225 may also be utilized in conjunction with a distributed computing environment where tasks are performed by remote processing devices that are linked through a communications network. In a distributed computing environment, program modules may be located in both local and remote memory storage devices. Execution of the program modules may occur locally in a stand-alone manner or remotely in a client/server manner. Examples of such distributed computing environments include local area networks of an office, enterprise-wide computer networks, and the Internet. Additionally, the networks could communicate via wireless means or any of a variety of communication means while remaining within the spirit and scope of the present invention.

Referring back to FIG. 2A, optical markings 215 are placed on the flexible web substrate 210 and are utilized to determine web deformation and skew during the roll-to-roll process. The marks 215 can be simple tracking marks or complicated patterns e.g. a chevron pattern. The web position sensors 220 track optical marks 215 that are present on the flexible substrate 210 and send electrical signals to the computer system 225 based on the detected position of the optical marks 215.

In the embodiment of FIG. 2A, the sensors 220 include pairs of optical illumination source/detector combinations. The light reflected off the web is modulated by the presence of the chevron pattern and converted to electrical signals by an optical detector. Based on the frequency of the electronic modulations the speed and position of the web can be determined and by the phase difference between the two sensors tracking the lateral position of the web marks relative to sensor can be determined. By having numerous sensor pairs 220 and web mark tracks, the position and location of the web at multiple locations can be determined. From this information the relative stretch or compression of the web compared to the desired state of compression can be determined.

Computer software within the computer system 225 receives the electronic signals and determines the deformation and skew of the flexible web substrate 215. Consequently, the computer system 225 sends re-alignment signals to the controllable mechanical components 230 at which point the controllable mechanical components 230 realign the flexible web substrate 210 based on the detected deformation and skew of the flexible web substrate 210.

Figure 4:
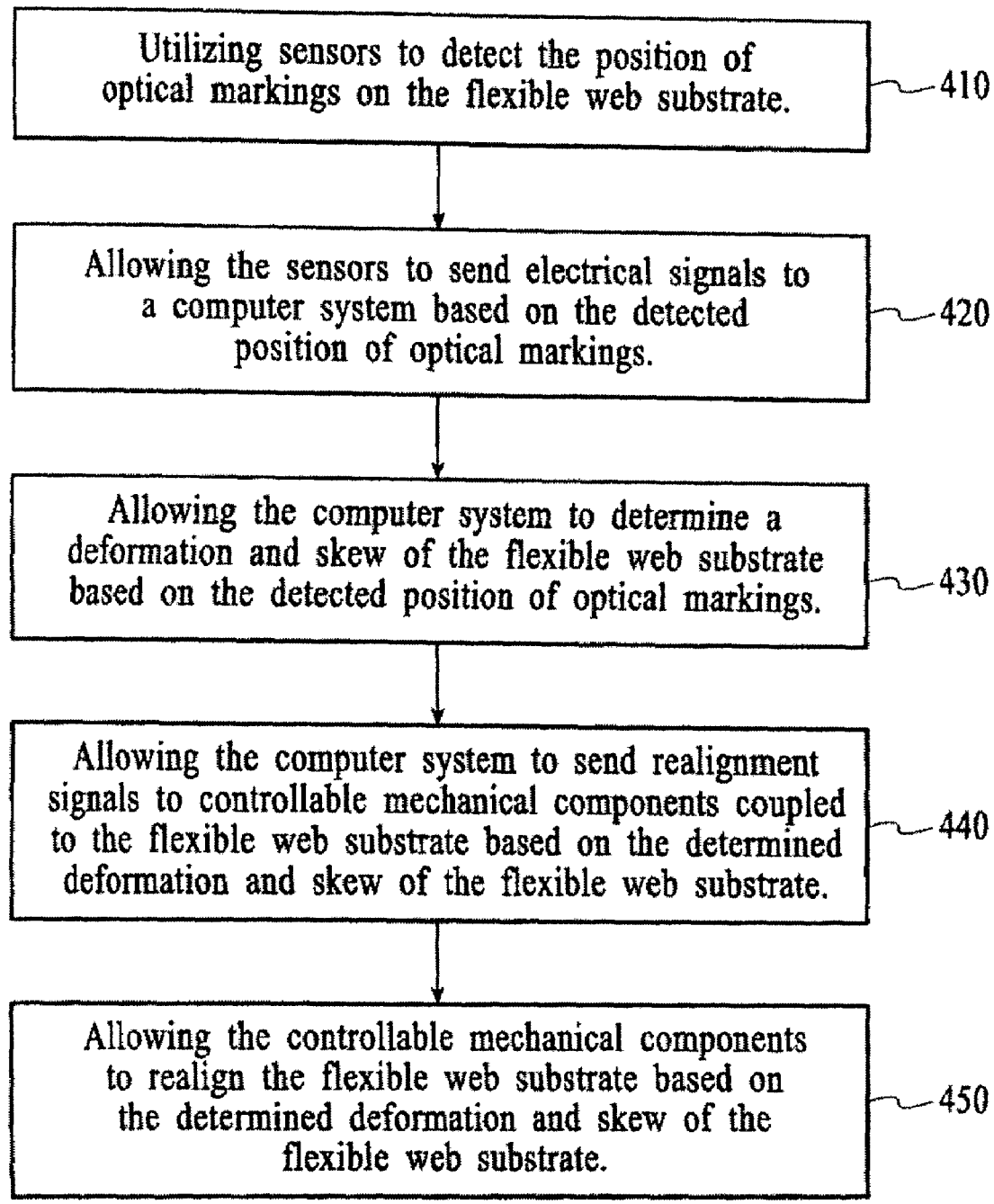
FIG. 4 is a more detailed flowchart of a method in accordance with an embodiment of the present invention.

FIG. 4 is a more detailed flowchart of a method in accordance with an embodiment of the present invention. A first step 410 includes utilizing sensors to detect the position of optical markings on the flexible web substrate. A second step 420 includes allowing the sensors to send electrical signals to a computer system based on the detected position of optical markings. A third step 430 includes allowing the computer system to determine a deformation and skew of the flexible web substrate based on the detected position of optical markings.

A fourth step 440 includes allowing the computer system to send realignment signals to controllable mechanical components coupled to the flexible web substrate based on the determined deformation and skew of the flexible web substrate. A final step 450 includes allowing the controllable mechanical components to realign the flexible web substrate based on the determined deformation and skew of the flexible web substrate.

Through the mechanical response of the web, changes in the web deformation are then sensed by the deformation state detectors and the process is completed. By appropriately determining the relation between the error and the sent realign signal, the process causes the web alignment to converge to the desired deformation state within certain error limits.

Referring back to FIG. 2A, the controllable mechanical components 230 are configured to realign the flexible web substrate 210 by inducing stress and pressure on the flexible web substrate thereby causing the flexible web substrate 210 to change position. This minimizes the error deviations, deformations and skews in the flexible web substrate 210 that are caused by variations in temperature, humidity, mechanical stress, etc.

Figure 5:
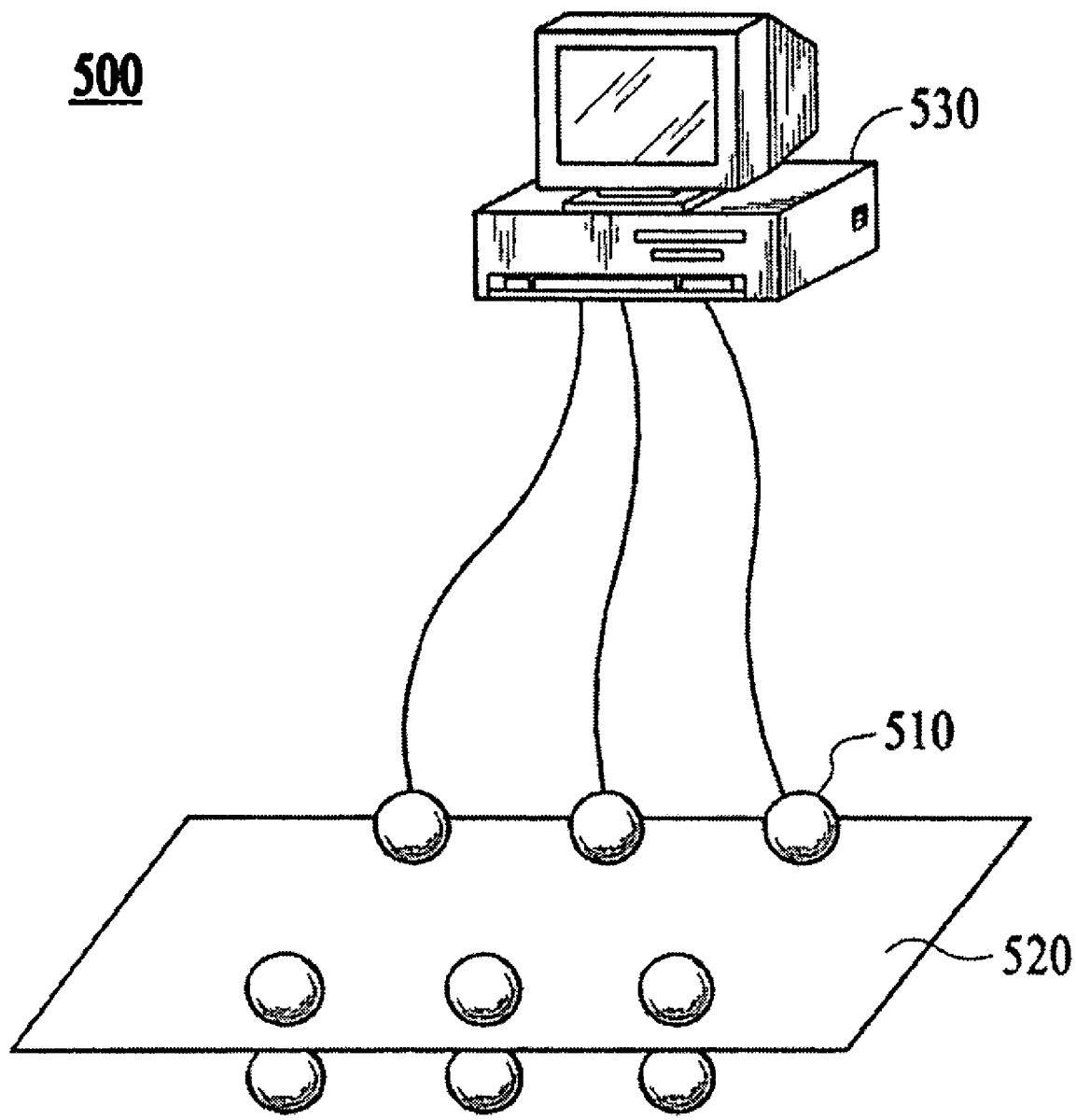
FIG. 5 is an illustration of a steerable disk configuration that could utilized in conjunction with an embodiment of the present invention.

In an embodiment of the present invention, the controllable mechanical components are steerable disks. FIG. 5 is an illustration of a steerable disk configuration 500. The configuration 500 shows a plurality of steerable disks 510 in contact with a flexible web substrate 520. The angle and speed of the steerable disks 510 are controlled by motors that can change the direction and the acceleration of the disk. Changing the angle causes various lateral forces to be transmitted to the web. These lateral forces in turn can be used to alter the deformation state of the web 520. The motors can be controlled using a computer system 530.

The computer system 530 sends realignment signals to the steerable disks 510 thereby causing the steerable disks 510 to exert a compensatory stress on the flexible web substrate 520 to account for any detected deformation and skew. One aspect of this embodiment that requires special care is that the steering angle should be changed only if the web is moving—otherwise nonplanar deformations will result. Hence complex calculations may be necessary to derive optimal steering protocols that minimize deformation errors.

Figure 6:
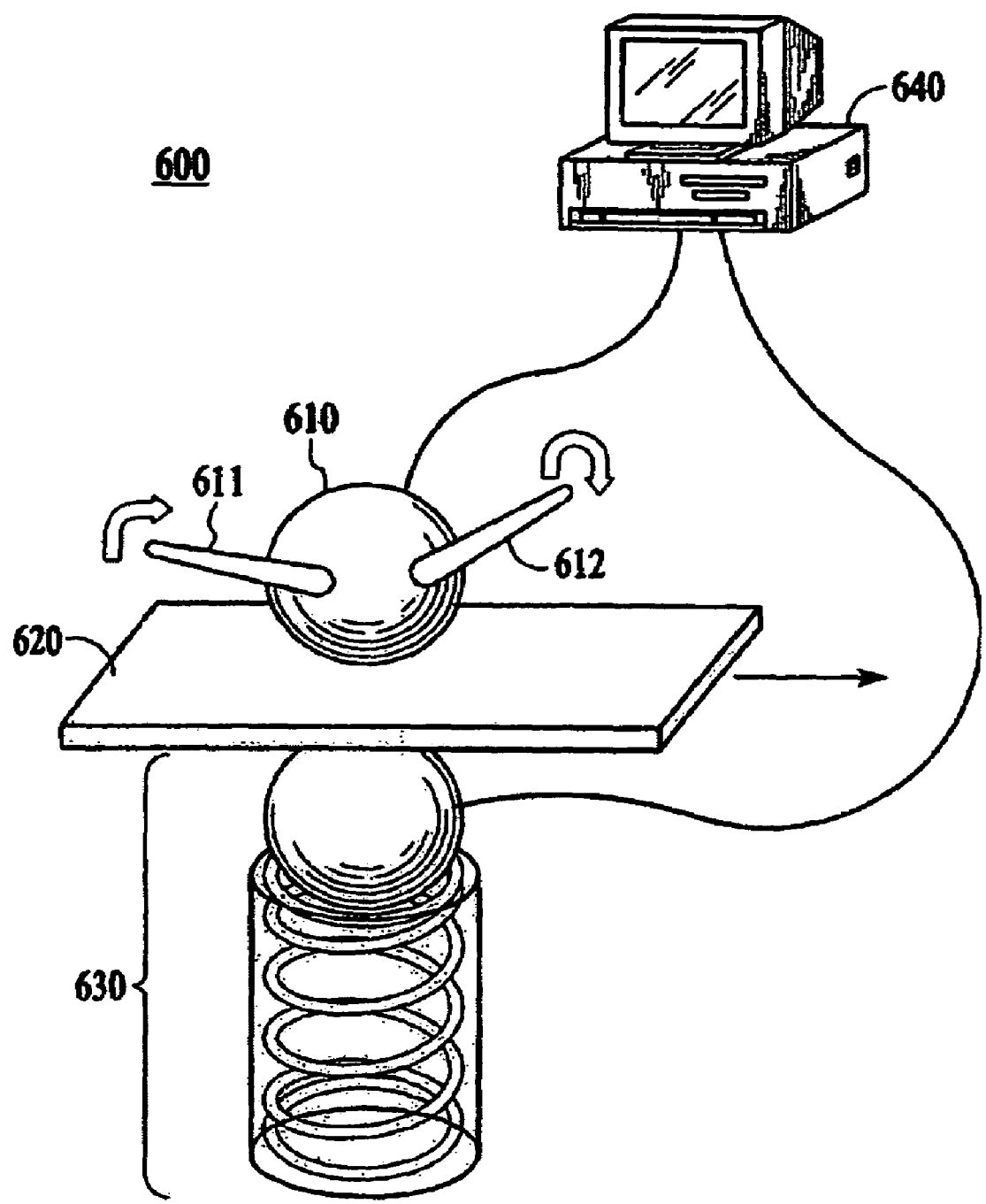
FIG. 6 is an illustration of a spherical nip configuration that could be utilized in conjunction with an embodiment of the present invention.

In an alternate embodiment, the controllable mechanical components are equatorially driven spheres referred to as spherical nips. The implementation of spherical nips avoids some of the more complex calculations of the previous embodiment. FIG. 6 is an illustration of a spherical nip configuration 600 that could be utilized in conjunction with an embodiment of the present invention. The configuration 600 shows a spherical nip 610 that is in contact with a flexible web substrate 620. The spherical nip 610 includes motorized equatorial drives 611, 612 that rotate the spherical nip 610 in the desired direction of motion to impart arbitrary point displacements to the flexible web substrate 620. Also shown in configuration 600 is a spring-loaded counter roller 630.

The spring-loaded counter roller 630 provides a perpendicular force to the spherical nip 610 and is designed to prevent slippage of the spherical nip 610 and increase the forces that can be imparted to the web. The spherical nip 610 is electronically coupled to a computer system 640. Accordingly, the computer system 640 sends realignment signals to the spherical nip 610 thereby causing the spherical nip 610 and the spring-loaded counter roller 630 to exert a compensatory stress on the flexible web substrate 620 to account for any detected deformation and skew.

Figure 7:
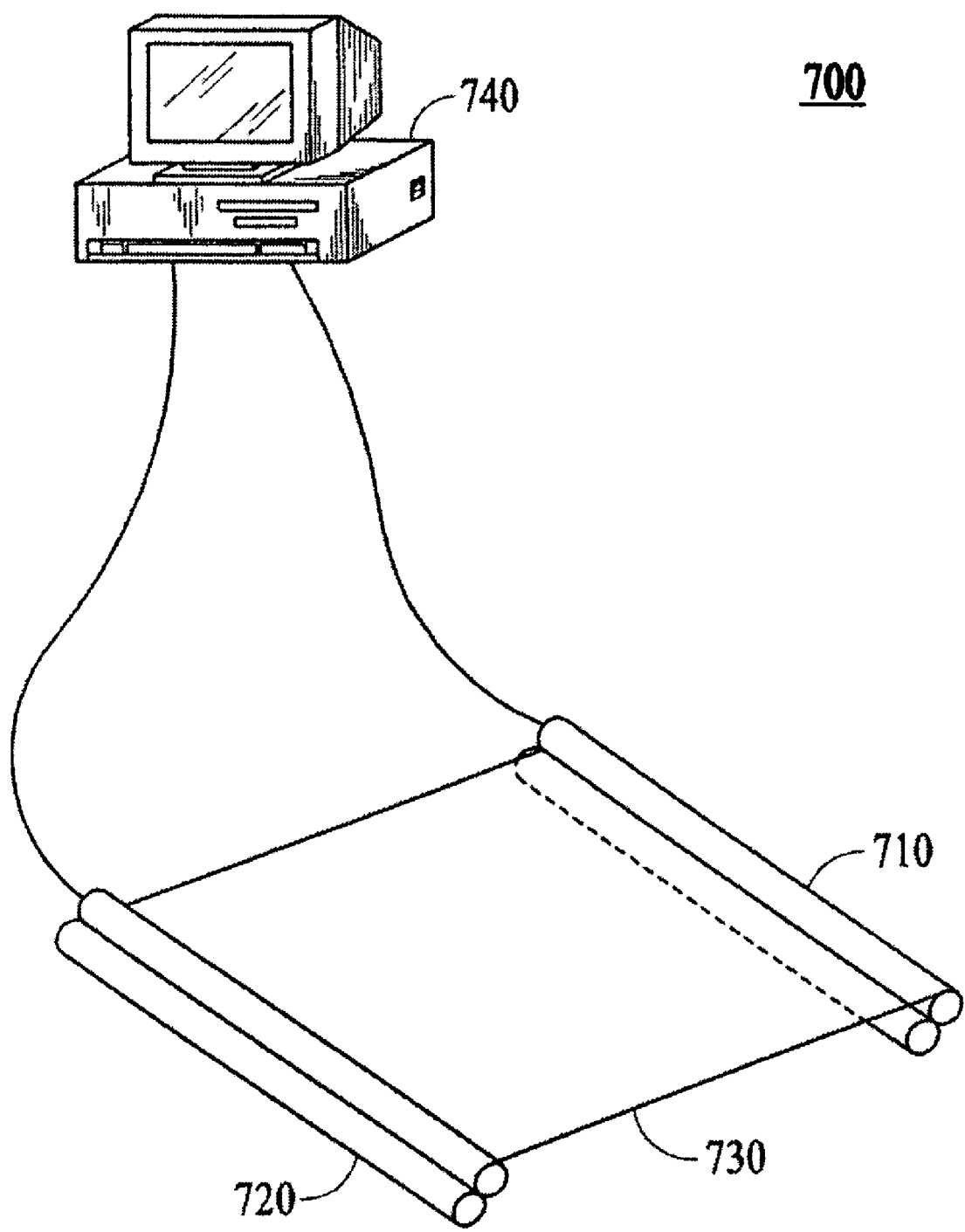
FIG. 7 is an illustration of a mechanical cross-roller configuration that could be utilized in conjunction with an embodiment of the present invention.

In yet another alternate embodiment, the controllable mechanical components include pairs of mechanical rollers (a drive roller and counter roller) whose axes of rotation can be varied with respect to those other roller pairs. FIG. 7 is an illustration of a mechanical cross-roller configuration 700 that could be utilized in conjunction with an embodiment of the present invention. The configuration 700 shows mechanical cross-rollers 710, 720 that drive a flexible web substrate 730. The axes of rotation of the 710 roller pair can be varied with respect to the axes of rotation of the 720 roller pair. Mechanical cross-rollers 710, 720 can impart lateral displacements and tensioning of the flexible web substrate 730 based on the angle, position and relative speed of the roller pair 710 with respect to the 720 roller pair. The motors controlling the speed, position and angle of the mechanical cross-rollers 710, 720 are electronically coupled to a computer system 740. Accordingly, the computer system 740 sends realignment signals to the mechanical cross-rollers 710, 720 thereby causing the mechanical cross-rollers 710, 720 to exert a compensatory stress on the flexible web substrate 730 to account for any detected deformation and skew.

Varying embodiments of a method and system for correcting web deformation during a roll-to-roll process have been disclosed. These embodiments include controllable mechanical components that are capable of dynamically adjusting the planarity of the web during the roll-to-roll process. By adjusting the web during the roll-to-roll process, the accuracy of the layer-to layer alignment of successive patterning steps is greatly increased thereby enabling the production of electronic structures with lower overlap capacitance and higher resolution.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed:

1. A method for correcting web deformation during a roll-to-roll process comprising:
   initiating a roll-to-roll process involving a flexible web substrate;
   detecting web deformation in the flexible web substrate during the roll-to-roll process; and
   dynamically correcting the flexible web substrate based on the detected web deformation wherein dynamically correcting the flexible web substrate comprises utilizing controllable mechanical components to correct the flexible web substrate based on the detected web deformation wherein the controllable mechanical components comprise spherical nips.

2. The method of claim 1 wherein detecting web deformation in the flexible web substrate includes:
   utilizing optical markings on the flexible web substrate to detect the web deformation;
   comparing the detected web deformation with a desired deformation;
   generating an error signal based on the comparison; and
   generating a correction signal to be utilized to dynamically correct the flexible web substrate.

3. The method of claim 1 wherein the controllable mechanical components include steerable disks.

4. The method of claim 1 wherein each spherical nip includes a spring loaded counter roller.

5. The method of claim 1 wherein the controllable mechanical components include mechanical cross-rollers.

6. A system for correcting web deformation during a roll-to-roll process comprising:
   means for initiating a roll-to-roll process involving a flexible web substrate;
   means for detecting web deformation in the flexible web substrate during the roll-to-roll process; and
   means for utilizing controllable mechanical components wherein the controllable mechanical components comprise spherical nips to dynamically correct the flexible web substrate based on the detected web deformation.

7. The system of claim 6 wherein the means for detecting web deformation in the flexible web substrate includes:
   means for utilizing optical markings on the flexible web substrate to detect the deformation;
   means for comparing the detected web deformation with a desired deformation;
   means for generating an error signal based on the comparison; and means for generating a correction signal to be utilized to dynamically correct the flexible web substrate.

8. The system of claim 6 wherein the controllable mechanical components include steerable disks.

9. The system of claim 6 wherein each spherical nip includes a spring loaded counter roller.

10. The system of claim 6 wherein the controllable mechanical components include mechanical cross-rollers.

11. A roll-to-roll processing system comprising:
    a web rolling mechanism;
    a flexible web substrate coupled to the web rolling mechanism;
    a plurality of sensors configured to dynamically detect deformation in the flexible web substrate;
    at least one controllable mechanical component coupled to the flexible web substrate wherein the at least one controllable mechanical component comprises a spherical nip; and
    a computer system coupled to the plurality of sensors and the at least one controllable mechanical component wherein the computer system includes logic for detecting web deformation in the flexible web substrate; and dynamically correcting the flexible web substrate based on the detected deformation.

12. The system of claim 11 wherein the logic for detecting deformations in the flexible web substrate includes logic for:
    utilizing optical markings on the flexible web substrate to detect the deformation;
    comparing the detected web deformation with a desired deformation;
    generating an error signal based on the comparison; and
    generating a correction signal to be utilized to dynamically correct the flexible web substrate.

13. The system of claim 11 wherein the logic for dynamically correcting the flexible web substrate comprises logic for:

utilizing the at least one controllable mechanical component to correct the flexible web substrate based on the detected web deformation.

14. The system of claim 13 wherein the at least one controllable mechanical component includes steerable disks.

15. The system of claim 13 wherein the at least one controllable mechanical component includes mechanical cross-rollers.

16. The system of claim 11 wherein the spherical nip includes a spring loaded counter roller.

17. A computer program product for correcting web deformation during a roll-to-roll process wherein the computer program product includes a computer usable medium having computer readable program means for causing a computer to perform the steps of:
    initiating a roll-to-roll process involving a flexible web substrate;
    detecting web deformation in the flexible web substrate during the roll-to-roll process; and
    dynamically correcting the flexible web substrate based on the detected web deformation wherein dynamically correcting the flexible web substrate comprises utilizing controllable mechanical components to correct the flexible web substrate based on the detected web deformation wherein the controllable mechanical components comprise spherical nips.

18. The computer program product of claim 17 wherein web detecting deformation in the flexible web substrate includes:
    utilizing optical markings on the flexible web substrate to detect the deformation;
    comparing the detected web deformation with a desired deformation;
    generating an error signal based on the comparison; and
    generating a correction signal to be utilized to dynamically correct the flexible web substrate.

19. A method for correcting web deformation during a roll-to-roll process comprising:
    utilizing optical markings on a flexible web substrate to detect the deformation in the flexible substrate;
    comparing the detected deformation with a desired deformation;
    generating an error signal based on the comparison; and
    generating a correction signal to be utilized to dynamically correct the flexible web substrate; and
    dynamically correcting the flexible web substrate based on the correction signal wherein dynamically correcting the flexible web substrate comprises utilizing controllable mechanical components to correct the flexible web substrate based on the detected web deformation wherein the controllable mechanical components comprise spherical nips.

20. The method of claim 19 wherein the controllable mechanical components include steerable disks.

21. The method of claim 19 wherein each spherical nip includes a spring loaded counter roller.

22. A method for correcting web deformation during a roll-to-roll process comprising:
    initiating a roll-to-roll process involving a flexible web substrate;
    detecting web deformation in the flexible web substrate during the roll-to-roll process; and
    utilizing controllable mechanical components to connect the flexible web substrate based on the detected web deformation wherein the controllable mechanical components include spherical nips wherein each spherical nip includes a spring loaded counter roller.

* * * * *